(12) United States Patent
Fatimi et al.

(10) Patent No.: US 11,176,849 B2
(45) Date of Patent: Nov. 16, 2021

(54) PUMPING HEART SIMULATOR

(71) Applicant: The Aga Khan University, Karachi (PK)

(72) Inventors: Saulat Hasnain Fatimi, Karachi (PK); Mohammad Bin Pervez, Karachi (PK); Charles Docherty, Karachi (PK)

(73) Assignee: The Aga Khan University, Karachi (PK)

( * ) Notice: Subject to any disclaimer, the term of this patent is extended or adjusted under 35 U.S.C. 154(b) by 222 days.

(21) Appl. No.: 16/219,163

(22) Filed: Dec. 13, 2018

(65) Prior Publication Data
US 2020/0135057 A1 Apr. 30, 2020

(30) Foreign Application Priority Data
Oct. 29, 2018 (PK) .................................. 738/2018

(51) Int. Cl.
| | |
|---|---|
| *G09B 23/30* | (2006.01) |
| *G09B 23/32* | (2006.01) |
| *G16H 50/50* | (2018.01) |
| *G09B 23/28* | (2006.01) |
| *A61M 60/148* | (2021.01) |

(52) U.S. Cl.
CPC ........... *G09B 23/303* (2013.01); *G09B 23/32* (2013.01); *G16H 50/50* (2018.01); *A61M 60/148* (2021.01); *G09B 23/288* (2013.01)

(58) Field of Classification Search
CPC .... G09B 23/288; G09B 23/30; G09B 23/303; G09B 23/32; G16H 50/50; A61M 60/148
USPC ........ 446/265, 267, 268, 272; 434/265, 267, 434/268, 272
See application file for complete search history.

(56) References Cited

U.S. PATENT DOCUMENTS

| | | | | |
|---|---|---|---|---|
| 3,704,528 A | * | 12/1972 | Lewis ................... | G09B 23/30 434/268 |
| 4,662,355 A | * | 5/1987 | Pieronne ............. | A61M 1/3639 600/17 |
| 4,756,705 A | * | 7/1988 | Beijbom ............. | A61M 1/3627 128/DIG. 3 |
| 5,620,326 A | * | 4/1997 | Younker ................ | G09B 23/28 434/268 |
| 5,634,797 A | * | 6/1997 | Montgomery ....... | G09B 23/286 434/268 |
| 5,807,737 A | * | 9/1998 | Schill ................... | A01N 1/0247 435/1.2 |

(Continued)

FOREIGN PATENT DOCUMENTS

| | | |
|---|---|---|
| JP | 6395609 | 9/2018 |
| WO | WO2018126254 | 7/2018 |

*Primary Examiner* — Joseph B Baldori
(74) *Attorney, Agent, or Firm* — Fish & Richardson P.C.

(57) ABSTRACT

A pumping heart simulator is described. The pumping heart simulator can include an inflow pump, an outflow pump, and a control apparatus. The inflow pump can have a first magnetic motor that facilitates flow of fluid from a bottom portion of a fluid reservoir to three inlet valves of a heart via the inflow pump. The outflow pump can have a second magnetic motor that facilitates flow of fluid from two outlet valves of the heart to a top portion of the fluid reservoir via the outflow pump. The control apparatus can alternately activate the first magnetic motor and the second magnetic motor. Related apparatuses, systems, methods, techniques and articles are also described.

17 Claims, 2 Drawing Sheets

(56) References Cited

U.S. PATENT DOCUMENTS

| | | | |
|---|---|---|---|
| 7,798,815 B2 | 9/2010 | Ramphal et al. | |
| 8,690,580 B2* | 4/2014 | Paronen | G09B 23/30 |
| | | | 434/267 |
| 9,183,763 B2* | 11/2015 | Carson | G09B 23/281 |
| 9,805,625 B2* | 10/2017 | Feins | G09B 23/306 |
| 10,755,601 B2* | 8/2020 | Okayama | G09B 23/285 |
| 2014/0370490 A1* | 12/2014 | Laizzo | A01N 1/0247 |
| | | | 435/1.2 |
| 2016/0027345 A1* | 1/2016 | Carson | G09B 23/30 |
| | | | 434/262 |
| 2016/0140878 A1* | 5/2016 | Fernandez | G09B 23/303 |
| | | | 434/268 |
| 2017/0051736 A1* | 2/2017 | Okayama | F04B 17/03 |
| 2017/0103682 A1* | 4/2017 | Okayama | G09B 9/00 |
| 2017/0116887 A1* | 4/2017 | Mchale | G09B 23/306 |
| 2018/0018904 A1* | 1/2018 | Okayama | G09B 23/286 |
| 2018/0108276 A1* | 4/2018 | Ishiyama | G09B 23/32 |
| 2019/0333413 A1* | 10/2019 | Bauer | G09B 23/303 |
| 2020/0160753 A1* | 5/2020 | Sadasivan | G09B 23/303 |
| 2021/0043113 A1* | 2/2021 | Sadasivan | G05D 7/0635 |

\* cited by examiner

202 CONNECTING FIRST MAGNETIC MOTOR OF INFLOW PUMP TO BOTTOM PORTION OF FLUID RESERVOIR

204 CONNECTING SECOND MAGNETIC MOTOR OF OUTFLOW PUMP TO TOP PORTION OF FLUID RESERVOIR

206 ACTUATING CONTROL APPARATUS THAT ALTERNATELY ACTIVATES FIRST MAGNETIC MOTOR AND SECOND MAGNETIC MOTOR

FIG. 2

PUMPING HEART SIMULATOR

RELATED APPLICATION

This disclosure claims priority to Pakistan Patent Application No. 738/2018, filed on Oct. 29, 2018, and entitled "Pumping Heart Simulator", the entire contents of which are hereby fully incorporated by reference.

TECHNICAL FIELD

The subject matter described herein relates to a pumping heart simulator to simulate diastolic and systolic phases of heart.

BACKGROUND

Various cardiac procedures require opening of a heart chamber, such as cannulation of the right atrium, cannulation of the aorta, bicaval cannulation, coronary artery bypass grafting, mitral valve replacement, aortic valve replacement, aortic root procedure, repair or minimally invasive surgery of the mitral valve and/or the tricuspid valve, maze procedure for atrial fibrillation, congenital open heart procedure, left ventricular assist device placement, and the like. The training opportunities available to medical residents, doctors, or other trainees for such procedures are inadequate because such training requires presence of a pumping heart. A pumping heart is often unavailable or scarce for various reasons such as discomfort in training newbies to avoid aggravating risks the procedure already imposes or scarcity of relevant patients.

One way to simulate a pumping heart can be to place a pneumatic balloon inside a cavity of the heart. However, placing such a mechanical component (i.e., the pneumatic balloon) inside the cavity of the heart obstructs access to anatomical parts (e.g., tissue) within such cavity, thereby imposing limits on training for procedures (e.g., intracardiac procedures or congenital cardiac surgeries) that require access to such anatomical parts. Moreover, such simulation does not involve blood or similar fluid, and accordingly does not teach navigation through the anatomy in the presence of blood. Therefore, there exists a need for a simulator that simulates a pumping heart in the presence of simulated blood and without inserting any mechanical components inside the cavity of the heart.

SUMMARY

In one aspect, a pumping heart simulator is described. The pumping heart simulator can include an inflow pump, an outflow pump, and a control apparatus. The inflow pump can have a first magnetic motor that facilitates flow of fluid from a bottom portion of a fluid reservoir to three inlet valves of a heart via the inflow pump. The outflow pump can have a second magnetic motor that facilitates flow of fluid from two outlet valves of the heart to a top portion of the fluid reservoir via the outflow pump. The control apparatus can alternately activate the first magnetic motor and the second magnetic motor.

In another aspect, a method of configuring the pumping heart simulator is described. A first magnetic motor of an inflow pump can be connected to a bottom portion of a fluid reservoir. The first magnetic motor can facilitate flow of fluid from the bottom portion of the fluid reservoir to three inlet valves of a heart via the inflow pump. A second magnetic motor of an outflow pump can be connected to a top portion of the fluid reservoir. The second magnetic motor can facilitate flow of fluid from two outlet valves of the heart to a top portion of the fluid reservoir via the outflow pump. A control apparatus can be actuated to alternately activates the first magnetic motor and the second magnetic motor.

Related apparatuses, systems, methods, techniques and articles are also described and within the scope of this disclosure.

The details of one or more variations of the subject matter described herein are set forth in the accompanying drawings and the description below. Other features and advantages of the subject matter described herein will be apparent from the description, the drawings, and the claims.

BRIEF DESCRIPTION OF DRAWINGS

FIG. 2 illustrates a method of configuring the pumping heart simulator, in accordance with some implementations of the current subject matter.

DETAILED DESCRIPTION

Figure 1:
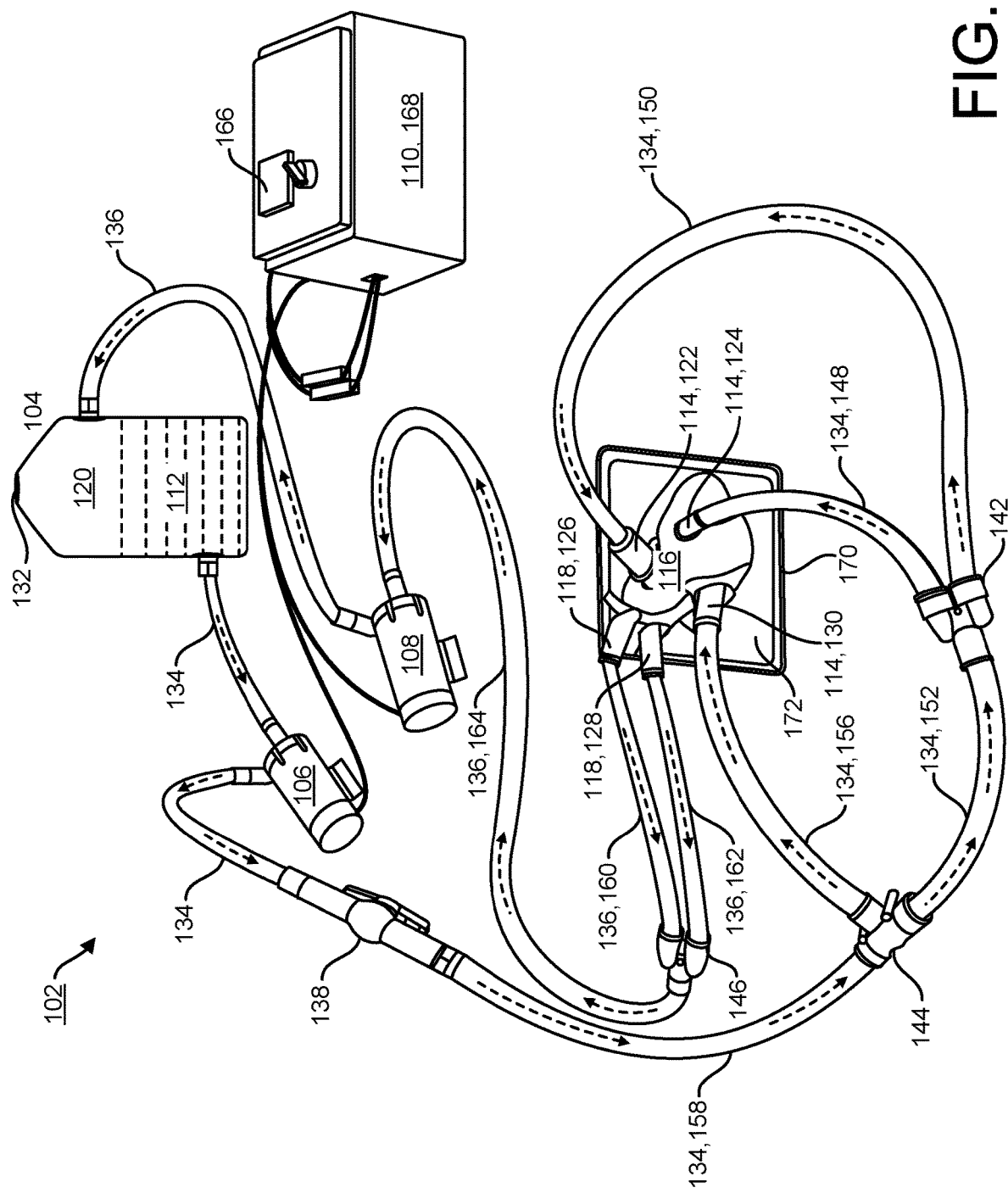
FIG. 1 illustrates a pumping heart simulator, in accordance with some implementations of the current subject matter.

FIG. 1 illustrates a pumping heart simulator 102. The pumping heart simulator 102 can include a fluid reservoir 104, an inflow pump 106, an outflow pump 108, and a control apparatus 110. The inflow pump 106 can have a first magnetic motor that facilitates flow of fluid from a bottom portion 112 (i.e., portion that has fluid) of the fluid reservoir 104 to three inlet valves 114 of a heart 116 via the inflow pump 106. The first magnetic motor is not shown in the drawing, as it is concealed within the casing for the inflow pump 106. The outflow pump 108 can have a second magnetic motor that facilitates flow of fluid from two outlet valves 118 of the heart 116 to a top portion 120 (i.e., portion that has air) of the fluid reservoir 104 via the outflow pump 108. The second magnetic motor is not shown in the drawing, as it is concealed within the casing for the outflow pump 108. The control apparatus 110 can alternately activate the first magnetic motor and the second magnetic motor.

The fluid reservoir 104 can be easily portable. The fluid reservoir 104 can be a container having a capacity of up to fifteen liters of fluid. While the fluid reservoir 104 is described as a part of the pumping heart simulator 102, in some implementations the fluid reservoir 104 may be external to the pumping heart simulator 102.

Any of the inflow pump 106 and the outflow pump 108 can be any positive displacement pump, any impulse pump, any velocity pump, any gravity pump, any steam pump, any valveless pump, and/or the like. Although the inflow pump 106 and the outflow pump 108 are shown as electric pumps, in alternate implementations any of those pumps can be powered by other means of power, such as wind power, solar power, any other form of power, and/or any combination thereof.

The control apparatus 110 can control the functionality of the inflow pump 106 and the outflow pump 108 by controlling the motors within the respective pumps. Besides controlling the motors, the control apparatus 110 can include sensors to protect the inflow pump 106 and the outflow pump 108 from stress or damage, and pilot devices for the user to control the inflow pump 106 and the outflow pump 108, as described below.

The sensors to protect the inflow pump 106 and the outflow pump 108 from stress or damage can include at least one motor overload sensor, at least one temperature sensor, at least one flow sensor, and at least one pressure sensor. The activation of an motor overload sensor can indicate that the motor of the pump 106/108 is drawing excessive current (i.e., current beyond a preset threshold). The activation of a temperature sensor can indicate that the temperature within the motor of the pump 106/108 is high (i.e., temperature beyond a preset threshold), and that the motor may be getting overheated. The activation of a flow sensor can indicate that the flow rate of fluid entering and/or exiting the pump 106/108 is abnormal (i.e., flow rate outside of a preset range). The activation of the pressure sensor can indicate that the fluid pressure within the pump 106/108 is abnormal (i.e., pressure outside of a preset range). When the sensor is activated, human intervention may be needed to rectify the error indicated by the activated sensor. Alternately, the control apparatus 110 can include electromechanical parts connected to the sensors such that those electromechanical parts can automatically be activated to rectify the detected error.

To enable a user to use the control apparatus 110, the control apparatus 110 can have main power controls, pump controls, and monitor controls. The main power control can be a disconnect switch. The pump controls can include a system off-on selector, manual-off-auto selector, level or pressure set-point, and/or speed control. The monitoring controls can include a running status monitor, one or more alarm status monitors, level or pressure monitor, and/or speed monitor. Each monitor can be one or more light emitting diodes of one or more colors. In some implementations, the user may need to be an authorized user, who can be authorized by inputting a username and password on the control apparatus 110.

The control apparatus 110 can be realized in digital electronic circuitry, integrated circuitry, specially designed application specific integrated circuits (ASICs), field programmable gate arrays (FPGAs) computer hardware, firmware, software, and/or combinations thereof.

The heart 116 can be a bovine heart. The use of a bovine heart can be beneficial for trainees who prefer not to work on porcine tissue, which is used in many wet laboratories, or a tissue of any animal besides cattle. Although a bovine heart is described, in alternate implementations the heart 116 can be a heart of any other animal. The three inlet valves 114 can correspond to a superior vena cava 122 of the heart 116, an inferior vena cava 124 of the heart 116, and a left atrium 130 of the heart 116. The two outlet valves 118 can correspond to an aorta 126 of the heart 116 and a pulmonary artery 128 of the heart 116. The valves described herein can be coupled to the corresponding anatomical parts by using cable ties.

The pulmonary venous openings of the heart can be closed with sutures. The sutures can be silk sutures, which can be advantageous due to their extreme pliability, ease of handling, and excellent knot strength. Although silk sutures is described, in alternate implementations catgut sutures and/or synthetic sutures can additionally or alternatively be used. The material to make synthetic sutures can include absorbables as well as non-absorbables. The absorbables can include polyglycolic acid, polylactic acid, MONOCRYL, polydioxanone, any other one or more absorbables, and/or any combination thereof. The non-absorbables can include nylon, polyester, polyvinylidene difluoride (PVDF), polypropylene, any other one or more non-absorbables, and/or any combination thereof.

The fluid reservoir 104 can have an opening 132 for air. The opening 132 can prevent undesirable pressure or temperature in the fluid reservoir 104. The bottom portion 112 of the fluid reservoir 104 can contain the fluid. The top portion 120 of the fluid reservoir 104 can contain air. As the amount of fluid and air in the fluid reservoir 104 may vary based on inflow and outflow, the height as well as volume of each of the top portion 120 and the bottom portion 112 can vary accordingly.

The pumping heart simulator 102 can include a first plurality of tubes 134, which can connect the inflow pump 106 with the bottom portion 112 of the fluid reservoir 104 and with the three inlet valves 114. The pumping heart simulator 102 can include a second plurality of tubes 136 connecting the outflow pump 108 with the top portion 120 of the fluid reservoir 104 and with the two outlet valves 118. The arrows shown within all the tubes can indicate the direction in which fluid flows there-through. Note the fluid may not flow in all the tubes simultaneously. The pumping heart simulator 102 can include a first set of one or more flow valves 138, which can control a flow of the fluid in the first plurality of tubes 134. The flow valve 138 can include an element that can be turned clockwise (or alternately anti-clockwise) to vary the flow within the tube on which the flow valve 138 is placed. In other implementations (not shown), the pumping heart simulator 102 can additionally or alternately include a second set of one or more flow valves to control a flow of the fluid in the second plurality of tubes 136.

The pumping heart simulator 102 can include a first three-way connector 142, a second three-way connector 144, and a third three-way connector 146. The first three-way connector 142 can couple a first tube 148 and a second tube 150 that are connected to the two inlet valves 114 with a third tube 152. The second three-way connector 144 can couple the third tube 152 with a fourth tube 156 connected to the third inlet valve of the three inlet valves 114 and with a fifth tube 158 connected to the inflow pump 106. The third three-way connector 146 can couple a sixth tube 160 connected to a first outlet valve of the two outlet valves 118 and a seventh tube 162 connected to a second outlet valve of the two outlet valves 118 with an eighth tube 164 connected to the outflow pump 108.

The tubes described herein can be made of plastic, rubber, any other suitable material, and/or any combination thereof. The term tube, as referred herein, can also be referred to as a pipe, hose, conduit, duct, and the like.

The first three-way connector 142 can be a Y-shaped connector. The second three-way connector 144 can be a T-shaped connector. The third three-way connector 146 can be another Y-shaped connector. In an alternate implementation, the first three-way connector 142 can be any one of a first Y-shaped connector and a first T-shaped connector, the second three-way connector 144 can be any one of a second Y-shaped connector and a second T-shaped connector, and the third three-way connector 146 can be any one of a third Y-shaped connector and a third T-shaped connector.

The control apparatus 110 can deactivate the first magnetic motor (within the inflow pump 106) when second magnetic motor (within the outflow pump 108) is activated. The control apparatus 110 can deactivate the second magnetic motor (within the outflow pump 108) when the first magnetic motor (within the inflow pump 106) is activated.

The pumping heart simulator 102 can further include a timer 166 communicatively coupled to the control apparatus 110 via a wired or a wireless connection. The wireless connection can be one or more of local area network, internet, wide area network, metropolitan area network, BLUETOOTH network, infrared network, and any other communication network. While the timer 166 is shown as being physically attached to the control apparatus 110, in alternate implementations the timer 166 can be either detachable or permanently detached from the control apparatus 110. Although a single timer is shown as indicating times for activation and deactivation of both the first motor and the second motor, in alternate implementations separate timers can be used to indicate such times for the first motor and the second motor. Such multiple timers can be communicatively coupled to the control apparatus 110 in the same manner as a single timer. The control apparatus 110 can alternate between the activation of the first magnetic motor (within the inflow pump 106) and the activation of the second magnetic motor (within the outflow pump 108) every preset amount of time. The preset amount of time can be two seconds to create systolic and diastolic phases of a normally functional heart. Although two seconds is described, in another implementation the preset amount of time can have any fixed value between one second and three seconds to simulate other scenarios of a heart. In yet another implementation, the preset amount of time can have a value that can vary every time between one second and three seconds. In some implementations, an authorized user may be permitted to set the preset amount of time to any fixed value.

The timer 166 can be a mechanical timer, an electrochemical timer, or an electronic timer. The mechanical timer can use clockwork to measure time. The electromechanical timer can be a short-period bimetallic electromechanical timer, and electromechanical cam timer, and/or any other electromechanical timer. The short-period bimetallic electromechanical timer can use a thermal mechanism, with a metal finger made of strips of two metals (e.g., steel, bronze, or the like) with different rates of thermal expansion sandwiched together. The electromechanical cam timer can use a small synchronous alternating current (AC) motor turning a cam against a comb of switch contacts. The AC motor can be turned at an accurate rate by the alternating current. Gears can drive a shaft at the desired rate, and turn the cam. The electronic timer can have digital electronics, and/or either an analog or a digital display. The electronic timer can be implemented as a simple single-chip computer system. In some implementations, the electronic timer can be implemented in software. A controller of such software timer can use a programmable logic controller (PLC).

The casing for the control apparatus 110 can further include a power source 168 configured to power the control apparatus 110. The control apparatus 110 can, in turn, alternately power the first magnetic motor (within the inflow pump 106) and the second magnetic motor (within the outflow pump 108). The alternate activation of the first magnetic motor and the second magnetic motor can cause the heart 116 to pump the fluid to simulate diastolic and systolic phases of heart. The power source 168 can be a wired connection with an electrical socket (now shown).

Alternately, the power source 168 can be a battery. The battery can be one or more rechargeable batteries, such as one or more nickel cadmium batteries, one or more nickel metal hydride batteries, one or more lithium ion batteries, one or more small sealed lead acid batteries, and other one or more rechargeable batteries, or any combination thereof. The advantages of a nickel cadmium battery are long life and economical price. The advantage of a nickel metal hydride battery is absence of toxic metals in the battery, thereby such battery being environment friendly. The advantages of a lithium-ion battery are high-energy density and light weight. The advantage of a lead battery is economical price.

The fluid can include water and at least one of a red dye and a red ink. The combination of the water and the at least one of the red dye and the red ink can simulate blood. In some implementations, the fluid can further include some material, such as syrup, to increase viscosity (i.e., thickness and stickiness) until the viscosity is same as that of the blood or as desired. The pumping heart simulator 102 can further include a tray 170 with a rubber sheet 172, on which the heart 116 can be placed. In other words, the rubber sheet 172 can hold the heart 116. The tray 170 can be rigid such that the tray does not twist or turn with the placement of the heart 116 on the rubber sheet 172 of the tray 170.

The anatomical parts of the heart 116 can be coupled as leak-proof as possible with mechanical components such as valves by using cable ties, zip ties, or any other mechanical component used for coupling. However, there can still be some seepage of the fluid from heart 116. To avoid seeped fluid from accumulating on the tray 170, the pumping heart simulator 102 can further include a suction apparatus (not shown) that can suction the fluid that seeped from the heart 116 onto the tray 170. Prior to the suction, however, the amount of seeped fluid on the tray 170 can be measured to assess drainage during the simulated procedure or surgery. The suction apparatus can be coupled to the top portion 120 of the fluid reservoir 104 via a tube to deliver the suctioned fluid into the fluid reservoir 104. The suction apparatus can be a hand-held device (i.e., the suction apparatus can be configured to be held by a hand of a user of the suction apparatus).

The pumping heart simulator 102 described herein can provide many advantages. For example, the pumping heart simulator 102 can simulate a pumping heart in the presence of simulated blood, which helps trainees develop skills of navigating to the anatomy in real-like situations. Furthermore, the pumping heart simulator 102 can attain the pumping without inserting any mechanical components inside the cavity of the heart 116, thereby enabling training of cardiac procedures that require access to the cavity. The pumping heart simulator 102 can therefore be used to effectively train for cardiac procedures requiring opening of a heart chamber, such as cannulation of the right atrium, cannulation of the aorta, bicaval cannulation, coronary artery bypass grafting, mitral valve replacement, aortic valve replacement, aortic root procedure, repair or minimally invasive surgery of the mitral valve and/or the tricuspid valve, maze procedure for atrial fibrillation, congenital open heart procedure, left ventricular assist device placement, and the like. Additionally, the pumping heart simulator 102 can be portable, light in weight, and easy to configure and use.

FIG. 2 illustrates a method of configuring the pumping heart simulator 102. A first magnetic motor of an inflow pump 106 can be connected, at 202, to a bottom portion 112 of a fluid reservoir 104. The first magnetic motor can facilitate flow of fluid from the bottom portion 112 of the fluid reservoir 104 to three inlet valves 114 of a heart 116 via the inflow pump 106. A second magnetic motor of an outflow pump can be connected, at 204, to a top portion 120 of the fluid reservoir 104. The second magnetic motor can facilitate flow of fluid from two outlet valves 118 of the heart 116 to a top portion 120 of the fluid reservoir 104 via the outflow pump 108. A control apparatus can be actuated, at 206, to alternately activates the first magnetic motor and the second magnetic motor.

The connections between all components described herein can be made leak-free by using cable-ties, sealing materials such as glue, any other connection means, and/or any combination thereof.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

The subject matter described herein can be embodied in systems, apparatuses, methods, and/or articles. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claims.

What is claimed is:

1. A pumping heart simulator comprising:
a fluid reservoir comprising a first coupling at a first region of the fluid reservoir and a second coupling at a second region of the fluid reservoir;
a heart coupled to the fluid reservoir and having multiple valves;
an inflow pump connected to the second coupling and the heart, the inflow pump comprising a first motor configured to control movement of fluid from the second coupling of the fluid reservoir to three inlet valves of the heart;
an outflow pump connected to the first coupling and the heart, the outflow pump comprising a second motor configured to receive the fluid from two outlet valves of the heart and provide the fluid to the first coupling of the fluid reservoir; and
a control apparatus connected to the inflow pump and the outflow pump and configured to alternately activate the first motor and the second motor.

2. The pumping heart simulator of claim 1, wherein the heart is a bovine heart.

3. The pumping heart simulator of claim 1, wherein:
the three inlet valves correspond to a superior vena cava of the heart, an inferior vena cava of the heart, and a left atrium of the heart; and
the two outlet valves correspond to an aorta of the heart and a pulmonary artery of the heart.

4. The pumping heart simulator of claim 1, wherein pulmonary venous openings of the heart are closed with sutures.

5. The pumping heart simulator of claim 1, wherein:
the first region is located above the second region in the fluid reservoir; and
a top portion of the fluid reservoir adjacent to the first region comprises an opening for air.

6. The pumping heart simulator of claim 5, wherein:
the second region of the fluid reservoir is configured to store the fluid; and
the first region of the fluid reservoir contains air.

7. The pumping heart simulator of claim 1, further comprising:
a first plurality of tubes connecting the inflow pump with the second coupling of the fluid reservoir and with the three inlet valves; and
a second plurality of tubes connecting the outflow pump with the first coupling of the fluid reservoir and with the two outlet valves.

8. The pumping heart simulator of claim 7, further comprising:
a first set of one or more flow valves to control a flow of the fluid in the first plurality of tubes; and
a second set of one or more flow valves to control a flow of the fluid in the second plurality of tubes.

9. The pumping heart simulator of claim 7, further comprising:
a first three-way connector coupling a first tube and a second tube that are connected to two of the three inlet valves with a third tube;
a second three-way connector coupling the third tube with a fourth tube connected to a third inlet valve of the three inlet valves and with a fifth tube connected to the inflow pump; and
a third three-way connector coupling a sixth tube connected to a first outlet valve of the two outlet valves and a seventh tube connected to a second outlet valve of the two outlet valves with an eighth tube connected to the outflow pump.

10. The pumping heart simulator of claim 1, wherein:
the control apparatus is configured to deactivate the first motor when the second motor is activated; and
the control apparatus is configured to deactivate the second motor when the first motor is activated.

11. The pumping heart simulator of claim 1, further comprising:
a timer communicatively coupled to the control apparatus, the control apparatus configured to alternate between activation of the first motor and the activation of the second motor every preset amount of time.

12. The pumping heart simulator of claim 11, wherein the preset amount of time is two seconds.

13. The pumping heart simulator of claim 1, further comprising:
a power source configured to power the control apparatus, the control apparatus alternately powering the first motor and the second motor.

14. The pumping heart simulator of claim 1, wherein alternate activation of the first motor and the second motor causes the heart to pump the fluid.

15. The pumping heart simulator of claim 1, wherein the fluid comprises water and at least one of a red dye and a red ink, a combination of the water and the at least one of the red dye and the red ink simulating blood.

16. The pumping heart simulator of claim 1, further comprising:
a tray with a rubber sheet for holding the heart.

17. The pumping heart simulator of claim 16, further comprising:
a suction apparatus configured to suction the fluid that seeped from the heart onto the tray, the suction apparatus coupled to the first region of the of the fluid reservoir via a tube to deliver the fluid into the fluid reservoir, the suction apparatus configured to be held by a hand.

* * * * *